(12) United States Patent
De Letter et al.

(10) Patent No.: US 11,810,470 B2
(45) Date of Patent: Nov. 7, 2023

(54) ANALYSIS OF EVOKED EVENT-RELATED POTENTIAL DATA

(71) Applicant: UNIVERSITEIT GENT, Ghent (BE)

(72) Inventors: Miet De Letter, Balegem (BE); Pieter Van Mierlo, Sint-Amandsberg (BE); Patrick Santens, Balegem (BE)

(73) Assignee: UNIVERSITEIT GENT, Ghent (BE)

( * ) Notice: Subject to any disclaimer, the term of this patent is extended or adjusted under 35 U.S.C. 154(b) by 12 days.

(21) Appl. No.: 17/628,777

(22) PCT Filed: Jul. 30, 2020

(86) PCT No.: PCT/EP2020/071541
§ 371 (c)(1),
(2) Date: Jan. 20, 2022

(87) PCT Pub. No.: WO2021/019029
PCT Pub. Date: Feb. 4, 2021

(65) Prior Publication Data
US 2022/0262269 A1   Aug. 18, 2022

(30) Foreign Application Priority Data
Jul. 31, 2019   (EP) .................................... 19189396

(51) Int. Cl.
*G09B 19/00*   (2006.01)
*G16H 10/60*   (2018.01)
(Continued)

(52) U.S. Cl.
CPC ............ *G09B 19/00* (2013.01); *A61B 5/0006* (2013.01); *A61B 5/0022* (2013.01); *A61B 5/377* (2021.01); *G16H 10/60* (2018.01)

(58) Field of Classification Search
CPC .......... G09B 19/00; G16H 10/60; A61B 5/00; A61B 5/0006; A61B 5/0022; A61B 5/377
See application file for complete search history.

(56) References Cited

U.S. PATENT DOCUMENTS 5,813,862 A * 9/1998 Merzenich ............. G11B 31/00
704/211

FOREIGN PATENT DOCUMENTS

WO   2015031517 A1   3/2015
WO   2018160992 A1   9/2018

OTHER PUBLICATIONS

International Search Report with Written Opinion from PCT Application No. PCT/EP2020/071541, dated Oct. 9, 2020.

(Continued)

*Primary Examiner* — Timothy A Musselman
(74) *Attorney, Agent, or Firm* — WORKMAN NYDEGGER (57) ABSTRACT

A computer-implemented system for obtaining therapeutic rehabilitation guidelines for a patient suffering from aphasia includes an input means for receiving evoked event-related potential data obtained through electroencephalography of a patient. The evoked event-related potential data is evoked by providing at least one predetermined language paradigm to the patient and the evoked event-related potential data includes amplitude, latency and source information for the evoked event-related potentials. The system also has a processor for processing the evoked event-related potential data including evaluating whether one or more of an amplitude, latency or source are within normative values for the at least one predetermined language paradigm and deriving based thereon a therapy to be applied to the patient, and an output for outputting the therapy instructions to be applied to the patient suffering from aphasia.

17 Claims, 3 Drawing Sheets

(51) Int. Cl.
    *A61B 5/377*    (2021.01)
    *A61B 5/00*    (2006.01)

(56) References Cited

OTHER PUBLICATIONS

Extended Search Report from corresponding EP Application No. 19189396.5, dated Jan. 16, 2020.
Aerts, "Neurophysiological and Clinical Investigation of Phonological Input Processing in Non-Brain Damaged Individuals and Patients with Aphasia." PhD dissertation, Ghent University, Chapters 8-10, As early as Jan. 1, 2014, 243 pages.
Aerts et al., "Aphasia Therapy Early After Stroke: Behavioural and Neurophysiological Changes in the Acute and Post-Acute Phases", Aphasiology, vol. 29, No. 7, Jan. 6, 2015, pp. 845-871.

* cited by examiner

ANALYSIS OF EVOKED EVENT-RELATED POTENTIAL DATA

FIELD OF THE INVENTION

The present invention relates to the field of neurosciences and rehabilitation. More particularly, the present invention relates to methods and systems for assisting in diagnosis and therapy for aphasia using language evoked EEG signals.

BACKGROUND OF THE INVENTION

After a stroke, people often suffer from aphasia. Currently typically behavior diagnostics is performed for determining the optimum therapy to be provided.

WO2015/031517 describes a method for providing electrical stimulation to a user as a user performs a set of tasks during a time window, recording a signal stream characterizing a neurological state of the user and identifying based thereon a neurological state of the user. The method also includes modulating the electrical stimulation treatment based on the determined neurological state.

There is a need for an evidence-based tool.

SUMMARY OF THE INVENTION

It is an object of the present invention to provide methods and systems for assisting in diagnosis and/or personalized therapy for aphasia patients.

It is an advantage of embodiments of the present invention to provide methods and systems for patient-specific aphasia diagnosis and/or for determining a patient-specific rehabilitation therapy for aphasia in an evidence-based perspective.

It is an advantage of embodiments of the present invention that methods and systems are provided that give direction for therapy, e.g. constrained-induced therapy, by allowing monitoring of neuroplasticity of patients during recovery.

It is an advantage of embodiments of the present invention that methods and systems are provided allowing monitoring of neuroplasticity during recovery and/or rehabilitation. In other words, according to some embodiments, the evolution of the neuroplasticity over time for a patient may be followed.

It is an advantage of embodiments of the present invention that methods and systems are provided allowing to translate the results of language paradigm evoked EEG signals into an evidence-based diagnosis and/or rehabilitation advice.

It is an advantage of embodiments of the present invention that methods and systems are provided allowing diagnosis and/or accurate rehabilitation therapy for aphasia in an accurate manner as these methods and systems are based on EEG measurements, which allow accurately characterizing the aphasia of a patient.

It is an advantage of embodiments of the present invention that methods and systems are provided allowing follow up of an evolution of a patient suffering from aphasia, as well as adjusting of the provided therapy, by repeatedly performing the analysis of EEG results over time. It is an advantage that patients thus may obtain an improved and better dedicated therapy for the aphasia suffered.

It is an advantage of embodiments of the present invention that large parts of the methods, if not all, can be automated.

It is an advantage of embodiments of the present invention that the amount of time required for the therapist to diagnose and determine the appropriate therapy may be limited, e.g. to about 1 hour.

It is an advantage of embodiments of the present invention that use can be made of conventional EEG devices that are readily available.

It is an advantage of embodiments of the present invention that use can be made of conventional parameters derivable from EEG data, being the source location, the amplitude and the latency.

It is an advantage of embodiments of the present invention that the specific language paradigms used can be varied, e.g. depending on the type of aphasia suffered by the patient.

It is an advantage of embodiments of the present invention that the method also allows for comparing the EEG data with individual MRI data of the patient, e.g. MRI data generated in the first weeks after a stroke or in the context of differential diagnosis in patients with probable dementia.

The object is obtained by a system and/or method according to the present invention.

The present invention relates to a computer-implemented system for obtaining therapy rehabilitation guidelines/instructions for a patient suffering from aphasia, the system comprising an input means for receiving evoked event-related potential data obtained through electroencephalography of a patient, the evoked event-related potential data being evoked by providing at least one predetermined language paradigm to the patient and the evoked event-related potential data comprising amplitude, latency and source information for the evoked event-related potentials, the system further comprising a processor for processing the evoked event-related potential data comprising evaluating whether one or more of an amplitude, latency or source are within predetermined criteria, e.g. normative values, for said at least one predetermined language paradigm and deriving based thereon therapy guidelines to be applied to the patient, and an output means for outputting the therapy guidelines to be applied to the patient suffering from aphasia.

The output means may for example be a data output port, a speaker, a screen, a printing device, a data output line, an internal or external memory, etc.

The evoked event-related potential data may comprise amplitude, latency and source of a grand average evoked event-related potential for said evoked event-related potential data.

The processing may comprise evaluating whether the latency of said evoked event-related potential data is above a first predetermined value.

Deriving the therapy instructions to be applied to the patient may comprise evaluating if the latency of said evoked event-related potential data is above the first predetermined value and deriving based thereon to apply training on auditive working memory when the latency of said evoked event-related potential is above the first predetermined value.

The processing may comprise evaluating whether an amplitude of said evoked event-related potential data is above a second predetermined value. This step may be performed after evaluating the latency or prior evaluating the latency.

Deriving the therapy instructions to be applied to the patient may comprise evaluating if the amplitude of said evoked event-related potential data is below the second predetermined value and deciding based thereon to increase training intensity when the amplitude of said evoked event-related potential data is below the second predetermined value.

The processing may comprise evaluating whether the source is ipsilateral or contralateral homotope or non-homotope. This step may be performed after evaluating the latency and the amplitude, prior to evaluating the latency and the amplitude or in between evaluating the latency and the amplitude.

Deriving the therapy instructions to be applied to the patient may comprise applying constrained-induced therapy instructions in case the source is contralateral non-homotope.

It is an advantage of embodiments of the present invention that by processing the different parameters in the evoked event-related potential data an accurate therapy can be determined. In some embodiments, the evaluation of the different parameters may advantageously be done in a specific order.

The at least one predetermined language paradigm may be a set of predetermined language paradigms. Where in embodiments of the present invention reference is made to a set of predetermined language paradigms, reference is made to at least two predetermined language paradigms.

The predetermined language paradigms may comprise one or more phonological tasks, semantic tasks and/or syntactic tasks. The predetermined language paradigms may in one example be paradigms testing a phonological input lexicon decision and/or testing a phonological preattentive/attentive analysis decision.

The output means may be adapted for providing an indication whether or not Constrained-induced therapy is to be applied to the patient.

The input means may be a data input port configured for receiving the evoked event-related potential data as data from a remote source.

The processor may be positioned at a physically remote position from the patient and wherein the system furthermore comprises a transmission means for transmitting the evoked event-related potential data over a network.

The input means may comprise an EEG recording device.

The present invention also relates to a computer-implemented method for obtaining therapeutic rehabilitation guidelines for a patient suffering from aphasia, the method comprising obtaining evoked event-related potential data obtained through electroencephalography of a patient, the evoked event-related potential data being evoked by providing at least one predetermined language paradigm to the patient and the evoked event-related potential data comprising amplitude, latency and source information for the evoked event-related potentials, processing the evoked event-related potential data comprising evaluating whether one or more of an amplitude, latency or source are within predetermined criteria for said at least one predetermined language paradigm and deriving based thereon therapy instructions to be applied to the patient, and outputting the therapy instructions to be applied to the patient suffering from aphasia.

Said processing may comprise evaluating whether a latency of said evoked event-related potential data is above a first predetermined value.

Said processing may comprise evaluating whether an amplitude of said evoked event-related potential data is above a second predetermined value.

Said processing may comprise evaluating whether the source is ipsilateral or contralateral homotope or non-homotope.

Evaluating the latency, the amplitude and the source may be performed in a predetermined order, although embodiments are not limited thereto. In one example, first latency may be evaluated, than amplitude may be evaluated and then source may be evaluated.

The present invention also relates to a computer program product comprising instructions which, when executed on a controller, inducing a method as described above.

Whereas systems and methods have been described whereby the evoked event-related potential data are being evoked by providing at least one predetermined language paradigm, the present invention also relates to methods and systems whereby the evoked event-related potential data are based on cognitive and motoric paradigms. The latter may for example be useful in patients with cognitive and/or motor decline e.g. after a stroke or in the context of neurodegeneration, infections or cerebral tumors.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Particular and preferred aspects of the invention are set out in the accompanying independent and dependent claims. Features from the dependent claims may be combined with features of the independent claims and with features of other dependent claims as appropriate and not merely as explicitly set out in the claims.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, in which.

In the drawings, the size of some of the elements may be exaggerated and not drawn on scale for illustrative purposes. The dimensions and the relative dimensions do not necessarily correspond to actual reductions to practice of the invention. Any reference signs in the claims shall not be construed as limiting the scope.

DETAILED DESCRIPTION OF ILLUSTRATIVE EMBODIMENTS

The present invention will be described with respect to particular embodiments and with reference to certain drawings but the invention is not limited thereto but only by the claims.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, directional terminology such as top, bottom, front, back, leading, trailing, under, over and the like in the description and the claims is used for descriptive purposes with reference to the orientation of the drawings being described, and not necessarily for describing relative positions. Because components of embodiments of the present invention can be positioned in a number of different orientations, the directional terminology is used for purposes of illustration only, and is in no way intended to be limiting, unless otherwise indicated. It is, hence, to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

It should be noted that the use of particular terminology when describing certain features or aspects of the invention should not be taken to imply that the terminology is being re-defined herein to be restricted to include any specific characteristics of the features or aspects of the invention with which that terminology is associated.

In the description provided herein, numerous specific details are set forth. However, it is understood that embodiments of the invention may be practiced without these specific details. In other instances, well-known methods, structures and techniques have not been shown in detail in order not to obscure an understanding of this description.

Whereas in embodiments of the present invention reference is made to a predetermined language paradigm, reference is made to phonological, semantic or grammatical input and/or output paradigms. These may be presented in an attentive and pre-attentive condition through the use of the oddball paradigm, commonly used in psychology research. The oddball paradigm consists of presentations of sequences of repetitive stimuli which are infrequently interrupted by a deviant stimulus whereby the reaction of the participant to this "oddball" stimulus is recorded.

Whereas in embodiments of the present invention reference is made to a grand average potential, reference is made to the potential resulting from an averaging of the EEG samples within or between subjects or paradigms.

Whereas in embodiments of the present invention reference is made to a homotopic contralateral area, reference is made to a mirror area of a normal area in the dominant hemisphere, while a non-homotopic contralateral area refers to any other area in the contralateral hemisphere.

In one aspect, the present invention relates to a computer-implemented system for obtaining therapeutic rehabilitation guidelines for a patient suffering from aphasia. The system comprises an input means for receiving evoked event-related potential data obtained through electroencephalography of a patient. Such an input means may be a data receiving port or may include an EEG data recording system. Further characteristics of a suitable EEG data recording system will be described with reference to a particular example. According to embodiments of the present invention, the evoked event-related potential data are being evoked by providing at least one predetermined language paradigm to the patient. The evoked event-related potential data comprise amplitude, latency and source information for the evoked event-related potentials. According to embodiments of the present invention, the system also comprises a processor for processing the evoked event-related potential data comprising evaluating whether one or more of an amplitude, latency or source are within predetermined criteria, e.g. normative values, for said at least one predetermined language paradigm. The processor may also be adapted for deriving based on the analysis a therapy to be applied to the patient. The system typically also comprises an output means for outputting the therapy instructions to be applied to the patient suffering from aphasia.

The system furthermore may be equipped with a memory for storing data and with a data transmission and receiving means for processing the information at a position different from the position where it is recorded. Such transmission may be based on any suitable transmission method, such as over the internet. The system may be setup as a web application, whereby the data is uploaded for processing at a different position, e.g. cloud based processing.

Further features and advantages will be shown in the exemplary embodiment shown below. One or more of these features may be included in embodiments of the present invention.

Figure 1:
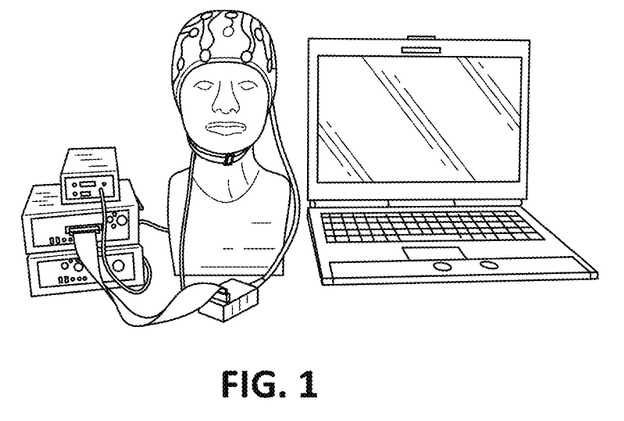
FIG. 1 and FIG. 2 illustrate an example of a system according to an embodiment of the present invention.
Figure 2:
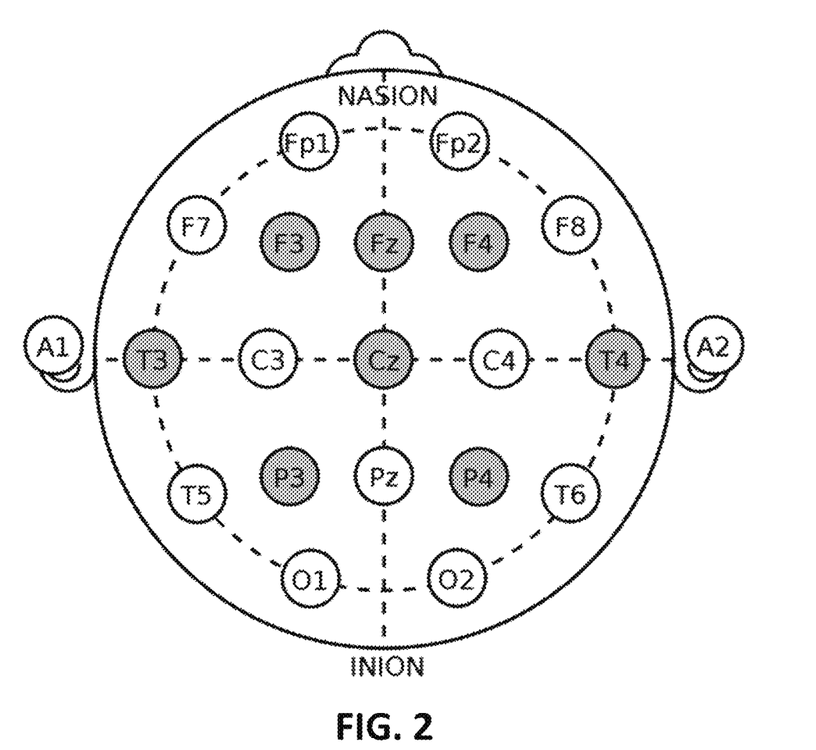

By way of illustration, embodiments of the present invention not being limited thereto, an example of a system for obtaining rehabilitation information is described below. The system comprises an input means for receiving evoked event-related potential data obtained through electroencephalography of a patient. The therapist examines the patient with a miniaturized EEG device and language paradigms for which predetermined criteria, e.g. normative values, have been developed. In the present example, the EEG-data were recorded using the Neuron-Spectrum-5 (EPM) registration software (Neurosoft, Moscow, Russia) and a Haube-S2 electrode cap including 20 Ag/AgCl-electrodes, namely Cz, Fz, P3, P4, F3, F4, T7, T8. The electrodes are placed on the scalp according to the international 10-20 system. An online linked ears-reference and a ground electrode on the forehead were used. In order to keep the electrode-impedance below 5 kΩ, an impedance-reducing gel (Electro-Gel™, Electro-Cap International, Inc.) was applied. A SynAmp (Neuroscan) amplifier was used and the data were digitized at a sampling rate of 500 Hz. The sample rate advantageously is 500 Hz or larger. The input system comprising the electrode cap and a computing device for recording is shown in FIG. 1. A particular example of electrode positions that can be used is shown in FIG. 2. Whereas the example given is made for an electrode configuration Cz, Fz, P3, P4, F3, F4, T7, T8, it will be clear for the person skilled in the art that alternative electrode configurations can be used, such as for example but not limited to configuration Fz, Cz, Pz, F7, F8, T3, T4, T5, T6. In the electrode configurations, advantageously at least positions Fz and Cz are included.

Although the processing could be performed locally, if the processor is located at the same local position, the system is certainly suitable for processing at another location. Therefore, the system may be adapted for sending the EEG data over a local network or over the internet or may be adapted for transferring the EEG data in any other way. The EEG data is analyzed (source localization, amplitude and latency time). The data is thereby checked with predetermined criteria, e.g. compared with normative data. A score may be generated. This algorithm performs the translation of online analyzed EEG-data into a rehabilitation guidelines.

Figure 3:
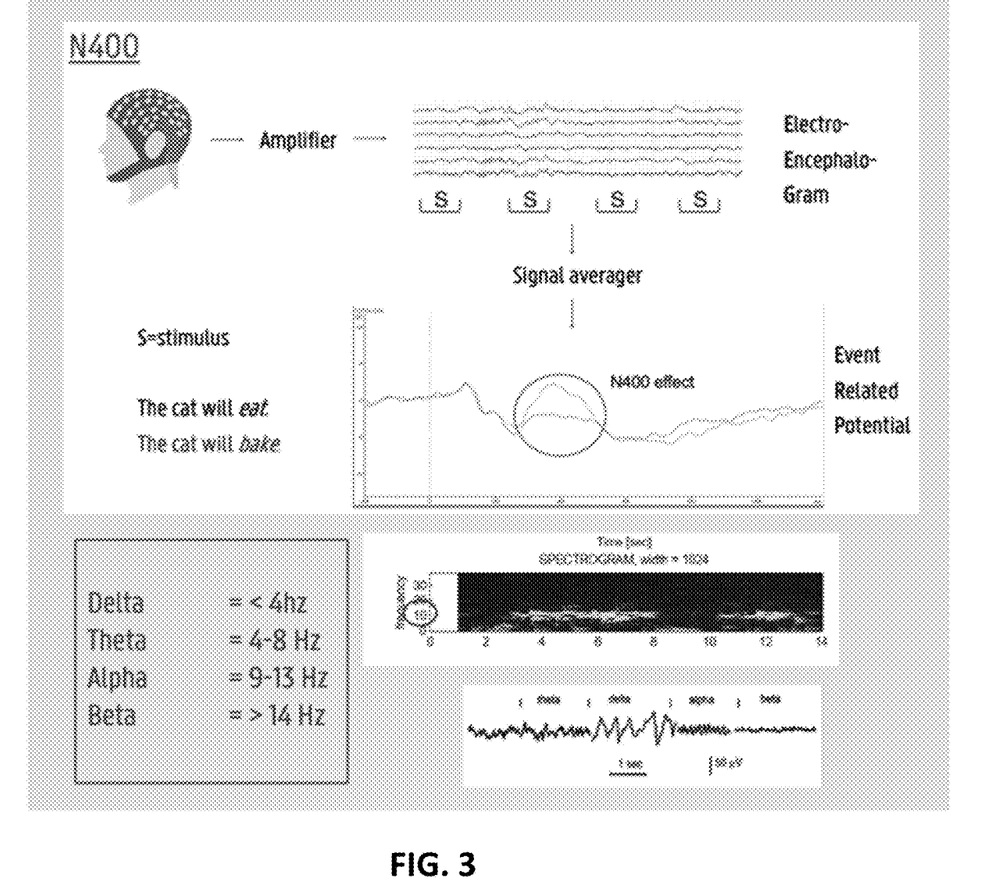
FIG. 3 illustrates a part of the processing performed by a processing system according to an embodiment of the present invention.
Figure 4:
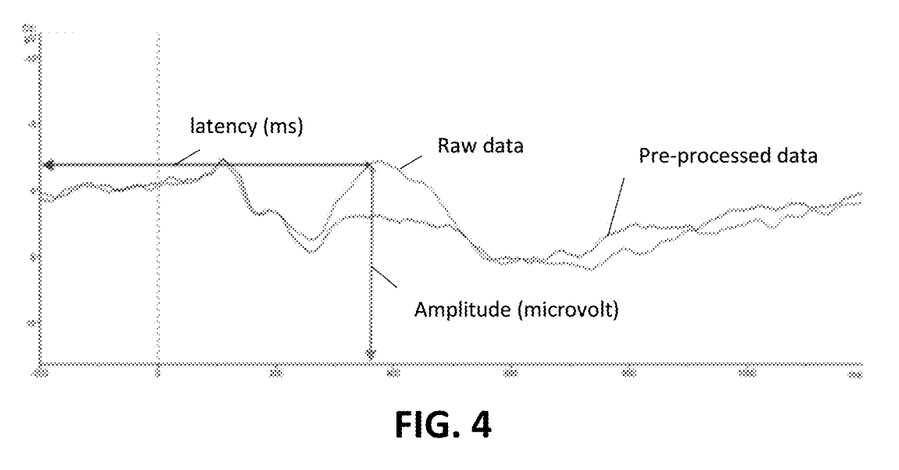
FIG. 4 illustrates determination of the latency and the amplitude as can be used in embodiments according to the present invention, wherein the first signal illustrates the standard stimuli and the second signal illustrates the deviant stimuli.

In the present example, pre-processing of the sample was applied prior to analyzing the latency, amplitude and source. Pre-processing may include identifying individual trials from a dataset, filtering and artifact rejections. The EEG pre-processing and analysis was performed using BrainVision Analyzer 2.1 (Brain Products, Munich, Germany). In some examples, pre-processing in different frequency ranges was applied. The EEG is described in terms of rhythmic activity. The rhythmic activity is subdivided into bands by frequency (bandwidths). The frequency bands are classified according to a nomenclature, with <4 Hz, 4-8 Hz, 9-131 Hz and >14 Hz be described as respectively the Delta, Theta, Alpha and Beta band. The latter is shown in FIG. 3. Frequency bands are extracted using spectral methods. The pre-processing in the present example also comprises applying a high-pass filter of 0.5 Hz (slope 12 dB/octave), a low-pass filter of 30 Hz (slope 48 dB/octave) and a notch filter of 50 Hz. Second, independent component analysis (ICA) is performed in order to detect and remove artefacts caused by eye-blinks and horizontal eye-movements. Third, standard and deviant trials are evaluated separately during segmentation. The epochs contain a baseline-period of 100 msec pre-stimulus, that is used for baseline correction. Data exceeding ±100 μV in the baseline-corrected epochs are semi-automatically rejected from further analysis. The average of standard trials on the one hand and deviant trials on the other hand are created. Analysis is performed on the difference waves (created by subtracting the standard trials from the deviant trials). Peak latencies and amplitudes are calculated semi-automatically in a component-specific time window, an example thereof being shown in FIG. 4. The measurement windows for the MMN, P300 and N400 are chosen based on a visual inspection of the data averaged across participants (Luck, 2014). Moreover, focus was given to the electrode positions for which predetermined criteria, e.g. normative data in healthy individuals (Aerts et al., 2013), were available (MMN: Cz and Fz; P300: Pz and N400: Cz). In the example, the processor also is adapted for evaluating whether the amplitude, latency and source are within predetermined criteria, e.g. normative values. It is to be noted that in the drawings provided, a + sign indicates that the values are within the normative values, whereas a − sign indicates that the values are outside the normative values. Typically a deviant latency is an increased latency. Typically a deviant amplitude is a decreased amplitude. Typically a deviant source corresponds with an activation of a contralateral non-homotope region. In general, if the latency, the amplitude are within predetermined values and the source is ipsilateral or contralateral homotope, training on the disturbed module itself is performed (if needed). If latency is prolonged, the therapy guideline includes training on the auditive working memory. If the amplitude is below the predetermined values, the therapy guidelines include increasing the intensity of the training. If the source is not ipsilateral or contralateral homotope, training is performed on compensation from the more intact modules. The amplitude, latency and source of the grand average evoked potential may be the determinants to the decision of starting Constrained-induced therapy or not. In one example, the at least one predetermined paradigm was a phonological pre-attentive and attentive analysis decision. Such a decision corresponds with an unattentive condition (MNM) in which patients have to watch a silent movie and ignore the stimuli and an attentive condition (P300) in which patients are instructed to push a button when hearing the deviant stimuli. In this example, the evaluation of the latency, the amplitude and the source is made as follows: If the latency is within the normal range, the amplitude is within the normal range and the source is ipsilateral or contralateral homotope, the therapy guideline includes focusing on auditive discrimination at phoneme level (if needed). If the latency is within the normal range, the amplitude is within the normal range and the source is contralateral non-homotope, the therapy guideline includes focusing on auditive discrimination, compensation for orthographical discrimination and prephonological training. If the latency is within the normal range, the amplitude is below a predetermined value and the source is ipsilateral or contralateral homotope, the therapy guideline includes focusing on auditive discrimination with an increased intensity. If the latency is within the normal range, the amplitude is below a predetermined value and the source is contralateral non-homotope, the therapy guideline includes focusing on auditive discrimination with an increased intensity, compensation for orthographical discrimination and prephonological training. If the latency is prolonged, the amplitude is within the normal range and the source is ipsilateral or contralateral homotope, the therapy guideline includes focusing on the auditive working memory at phoneme level and an auditive discrimination at phoneme level. If the latency is prolonged, the amplitude is within the normal range and the source is contralateral non-homotope, the therapy guideline includes focusing on the auditive working memory at phoneme level, at the auditive discrimination at phoneme level and on compensation for orthographical discrimination and prephonological training. If the latency is prolonged, the amplitude is below a predetermined value and the source is ipsilateral or contralateral homotope, the therapy guideline includes focusing on the auditive discrimination at phoneme level, at the auditive working memory with increased intensity. If the latency is prolonged, the amplitude is below a predetermined value and the source is contralateral non-homotope, the therapy guideline includes focusing on training of compensation for prephonology and orthographical discrimination, on the auditive working memory with increased intensity. In another example, the at least one predetermined paradigm was a phonological input lexicon requiring a lexical decision. In this example the evaluation of the latency, the amplitude and the source is made as follows. If the latency is within the normal range, the amplitude is within the normal range and the source is ipsilateral or contralateral homotope, the therapy guideline includes focusing on lexical decision (if needed). If the latency is within the normal range, the amplitude is within the normal range and the source is contralateral non-homotope, the therapy guideline includes focusing on a lexical decision, compensating for sem/lexicosem and orthograph input training. If the latency is within the normal range, the amplitude is below a predetermined value and the source is ipsilateral or contralateral homotope, the therapy guideline includes focusing on a lexical decision and on increasing the intensity. If the latency is within the normal range, the amplitude is below a predetermined value and the source is contralateral non-homotope, the therapy guideline includes focusing on a lexical decision and on increasing the intensity, while, compensating for sem/lexicosem and orthograph input training. If the latency is prolonged, the amplitude is within the normal range and the source is ipsilateral or contralateral homotope, the therapy guideline includes focusing on the auditive working memory at phoneme level and lexical decision. If the latency is prolonged, the amplitude is within the normal range and the source is contralateral non-homotope, the therapy guideline includes focusing on the auditive working memory at phoneme level, at a lexical decision and at compensating for sem/lexicosem and orthograph input training. If the latency is prolonged, the amplitude is below a predetermined value and the source is ipsilateral or contralateral homotope, the therapy guideline includes focusing on a lexical decision, at the auditive working memory with increased intensity. If the latency is prolonged, the amplitude is below a predetermined value and the source is contralateral non-homotope, the therapy guideline includes focusing at compensating for sem/lexicosem and orthograph input training, and at the auditive working memory with increased intensity.

More generally, the language paradigms used may contain phonological, semantic and syntactic tasks.

As indicated, the system in general also provides via output means for outputting the therapy guidelines to be applied to the patient suffering from aphasia. Based thereon, an individual patient rehabilitation report with personalized rehabilitation instructions typically is obtained.

The comparison with predetermined criteria, e.g. normative data, may be based on normative data determined upfront and by comparison with such stored data. Alternatively, the normative data also may be obtained based on data obtained using a neural network.

The advantage of the exemplary embodiment is that the full procedure can be finalized in about one hour. In this time, the recorded EEG data is translated into therapeutic guidelines for the individual patient. Another advantage is that the therapist is able to follow the neuroplasticity in the patient, by repeating the procedure on a regular basis.

In one embodiment, the system also may be adapted for comparing the estimated brain activation with an individual MRI of the patient, generated in the first weeks after stroke or in the context of differential diagnosis in patients with probable dementia. Such MRI typically will be available in the electronic patient file.

In some embodiments, in the processing the age of the patient also is taken into account. In one example, the age may be taken into account by using different predetermined criteria, e.g. normative data for discriminating phoneme for different decades. The patients thus were subdivided in age categories between 20 and 29, 30 and 39, 40 and 49, 50 and 59, 60 and 69 and 70 or above. In order to render the system automated, the input means therefore may also be programmed for obtaining the age of the patient involved. By way of illustration, embodiments not being limited thereto, examples of normative data for age-related phoneme discrimination of the amplitude and latency are given in the tables 1A and 1B.

TABLE 1A

Age-related normative data for phoneme discrimination of the amplitude Amplitudes (μV) for auditory phoneme discrimination.

| Age | | Attended (P300) | | | Unattended (MMN) | | |
|---|---|---|---|---|---|---|---|
| (y) | PC | M | SD± | Range | M (—) | SD± | Range (—) |
| 20-29 | PoA | 13.03 | 5.65 | 6.08-21.92 | 4.48 | 2.12 | 1.68-7.10 |
| | Voicing | 14.25 | 4.18 | 8.44-20.76 | 4.04 | 1.83 | 1.51-7.19 |
| | MoA | 13.24 | 5.39 | 5.63-21.78 | 3.41 | 2.07 | 0.59-5.80 |
| 30-39 | PoA | 14.08 | 5.58 | 4.10-22.50 | 2.87 | 1.35 | 1.47-5.42 |
| | Voicing | 14.74 | 5.77 | 8.54-28.57 | 3.81 | 1.05 | 2.08-5.76 |
| | MoA | 11.34 | 4.58 | 6.69-18.78 | 2.89 | 1.69 | 1.01-6.28 |
| 40-49 | PoA | 13.09 | 4.00 | 5.53-19.37 | 3.22 | 2.43 | 0.37-7.59 |
| | Voicing | 12.67 | 3.72 | 5.03-18.84 | 2.73 | 1.48 | 1.20-6.04 |
| | MoA | 11.63 | 4.07 | 3.52-17.00 | 2.51 | 1.53 | 0.24-5.36 |
| 50-59 | PoA | 12.19 | 4.78 | 5.48-23.19 | 3.98 | 1.46 | 2.03-6.94 |
| | Voicing | 11.89 | 5.99 | 4.07-22.96 | 3.64 | 1.41 | 1.24-5.72 |
| | MoA | 12.49 | 4.47 | 5.00-24.38 | 2.94 | 1.94 | 0.18-7.16 |
| 60-69 | PoA | 11.58 | 3.46 | 5.90-17.29 | 3.53 | 1.60 | 1.40-7.89 |
| | Voicing | 9.77 | 3.29 | 3.70-17.01 | 2.61 | 1.86 | 0.78-6.72 |
| | MoA | 10.07 | 3.80 | 1.87-15.69 | 2.42 | 1.71 | 0.04-5.66 |
| 70+ | PoA | 11.45 | 3.10 | 7.73-15.61 | 3.64 | 1.17 | 1.52-5.09 |
| | Voicing | 11.93 | 3.87 | 5.54-15.88 | 2.67 | 1.61 | 0.38-4.40 |
| | MoA | 12.04 | 5.31 | 5.57-18.44 | 1.91 | 1.83 | 0.05-5.16 | y = years; PC = phonemic contrast; PoA = place of articulation; MoA = manner of articulation; M = mean; SD = standard deviation; (—) = negative amplitudes.

TABLE 1B

Age-related normative data for phoneme discrimination of the latency
Latencies (ms) auditory phoneme discrimination.

| Age (y) | PC | Attended (P300) | | | Unattended (MMN) | | |
|---|---|---|---|---|---|---|---|
| | | M | SD± | Range | M | SD± | Range |
| 20-29 | PoA | 409 | 37.71 | 332-442 | 171 | 28.17 | 136-221 |
| | Voicing | 395 | 40.05 | 336-464 | 159 | 39.45 | 108-217 |
| | MoA | 385 | 58.01 | 312-466 | 159 | 13.04 | 136-178 |
| 30-39 | PoA | 398 | 46.75 | 338-488 | 153 | 24.39 | 129-193 |
| | Voicing | 385 | 41.34 | 338-454 | 166 | 50.59 | 89-237 |
| | MoA | 376 | 32.49 | 338-430 | 180 | 25.59 | 155-238 |
| 40-49 | PoA | 403 | 60.04 | 352-578 | 171 | 27.28 | 141-219 |
| | Voicing | 396 | 47.99 | 306-512 | 164 | 37.95 | 110-240 |
| | MoA | 376 | 33.51 | 328-434 | 174 | 28.47 | 133-234 |
| 50-59 | PoA | 418 | 50.11 | 310-518 | 184 | 38.57 | 133-242 |
| | Voicing | 416 | 53.18 | 350-546 | 173 | 40.00 | 89-232 |
| | MoA | 387 | 65.35 | 320-562 | 176 | 20.51 | 140-211 |
| 60-69 | PoA | 417 | 40.36 | 350-534 | 171 | 24.09 | 131-227 |
| | Voicing | 440 | 63.23 | 344-594 | 177 | 36.60 | 99-243 |
| | MoA | 400 | 50.69 | 304-508 | 190 | 26.10 | 135-241 |
| 70+ | PoA | 479 | 77.52 | 358-580 | 172 | 33.97 | 134-214 |
| | Voicing | 516 | 51.93 | 428-566 | 184 | 42.27 | 141-248 |
| | MoA | 451 | 53.79 | 396-550 | 182 | 16.43 | 158-202 | y = years; PC = phonemic contrast; PoA = place of articulation; MoA = manner of articulation; M = mean; SD = standard deviation.

In some embodiments, in the processing the gender of the patient also is taken into account. In order to render the system automated, the input means therefore may also be programmed for obtaining the gender of the patient involved. By way of illustration, embodiments not being limited thereto, examples of normative data for gender-related phoneme discrimination of the amplitude and latency, based on 71 healthy participants between 20 and 70 years old, are given in table 2.

TABLE 2 gender-related normative phoneme values for amplitude and latency

| | | | P300 PZ | | MMN CZ | |
|---|---|---|---|---|---|---|
| Measure | Sex | PC | M | SD | M (—) | SD |
| Amplitude (μV) | Men | PoA | 11.60 | 4.29 | 2.89 | 1.47 |
| | | Voicing | 12.02 | 4.12 | 3.28 | 1.44 |
| | | MoA | 10.81 | 4.81 | 2.52 | 1.52 |
| | Women | PoA | 15.45 | 3.99 | 4.25 | 2.02 |
| | | Voicing | 13.76 | 5.13 | 3.02 | 1.37 |
| | | MoA | 13.77 | 3.87 | 3.07 | 1.99 |
| Latency (ms) | Men | PoA | 423 | 49.37 | 180 | 31.43 |
| | | Voicing | 407 | 38.98 | 150 | 40.27 |
| | | MoA | 380 | 26.52 | 179 | 27.53 |
| | Women | PoA | 394 | 37.49 | 175 | 36.80 |
| | | Voicing | 394 | 38.79 | 177 | 51.56 |
| | | MoA | 380 | 46.78 | 169 | 27.28 |

PC phonemic contrast,
PoA place of articulation,
MoA manner of articulation,
(—) negative amplitudes In one aspect, the present invention also relates to a computer-implemented method for obtaining rehabilitation information for a patient suffering from aphasia. The method comprises obtaining evoked event-related potential data obtained through electroencephalography of a patient, the evoked event-related potential data being evoked by providing at least one predetermined language paradigm to the patient and the evoked event-related potential data comprising amplitude, latency and source information for the evoked event-related potentials. The method also comprises processing the evoked event-related potential data comprising evaluating whether one or more of an amplitude, latency or source are within predetermined criteria for said at least one predetermined language paradigm and deriving based thereon a therapy to be applied to the patient, and outputting the therapy to be applied to the patient suffering from aphasia. Further method steps may correspond with the functionality of the elements of the system described in the first aspect.

In still another aspect, the above described system embodiments may correspond with an implementation of the methods as described above, as a computer implemented invention in a processor. Such a system or processor—the processor also being discussed in functionality in an aspect described above—includes at least one programmable computing component coupled to a memory subsystem that includes at least one form of memory, e.g., RAM, ROM, and so forth. It is to be noted that the computing component or computing components may be a general purpose, or a special purpose computing component, and may be for inclusion in a device, e.g., a chip that has other components that perform other functions. Thus, one or more aspects of the present invention can be implemented in digital electronic circuitry, or in computer hardware, firmware, software, or in combinations of them. While a processor as such is prior art, a system or processor that includes the instructions to implement aspects of the methods is not prior art. The present invention thus also includes a computer program product which provides the functionality of any or part of the system as described in the first aspect. Similarly, the present invention relates to a controller or processor for performing the method aspects of the present invention, or for assisting therein, when such a processor or controller is coupled to an EEG recording system.

In yet another aspect, the present invention relates to a data carrier, e.g. a non-transitory data carrier, for carrying a computer program product as described in the previous aspect. Such a data carrier may comprise a computer program product tangibly embodied thereon and may carry machine-readable code for execution by a programmable processor. The present invention thus relates to a carrier medium carrying a computer program product that, when executed on computing means, provides instructions for executing any of the methods as described above. The term "carrier medium" refers to any medium that participates in providing instructions to a processor for execution. Such a medium may take many forms, including but not limited to, non-volatile media, and transmission media. Non-volatile media includes, for example, optical or magnetic disks, such as a storage device which is part of mass storage. Common forms of computer readable media include, a CD-ROM, a DVD, a blue ray disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

The invention claimed is:

1. A computer-implemented system for obtaining therapeutic rehabilitation guidelines for a patient suffering from aphasia, the system comprising:
    an input means for receiving evoked event-related potential data obtained through electroencephalography of a patient, the evoked event-related potential data being evoked by providing at least one predetermined language paradigm to the patient and the evoked event-related potential data comprising amplitude, latency and source information for the evoked event-related potentials,
    a processor for processing the evoked event-related potential data comprising evaluating whether one or more of an amplitude, latency or source are within predetermined criteria for said at least one predetermined language paradigm and deriving based thereon therapy instructions to be applied to the patient, and
    an output means for outputting the therapy instructions to be applied to the patient suffering from aphasia.

2. The system according to claim 1, wherein the evoked event-related potential data comprise amplitude, latency and source of a grand average evoked event-related potential for said evoked event-related potential data.

3. The system according to claim 1, wherein said processing comprises evaluating whether the latency of said evoked event-related potential data is above a first predetermined value.

4. The system according to claim 3, wherein said deriving the therapy instructions to be applied to the patient comprises deriving instructions to apply training on auditive working memory when the latency of said evoked event-related potential is above the first predetermined value.

5. The system according to claim 1, wherein said processing comprises evaluating whether the amplitude of said evoked event-related potential data is above a second predetermined value.

6. The system according to claim 5, wherein said deriving the therapy instructions to be applied to the patient comprises deriving instructions to increase training intensity when the amplitude of said evoked event-related potential data is below the second predetermined value.

7. The system according to claim 1, wherein said processing comprises evaluating whether the source is ipsilateral or contralateral homotope or non-homotope.

8. The system according to claim 7, wherein said deriving the therapy instructions to be applied to the patient comprises deriving instructions to apply constrained-induced therapy when the source is contralateral non-homotope.

9. The system according to claim 1, wherein said input means is adapted for obtaining information regarding the gender of the patient and wherein said predetermined criteria are gender-specific normative values.

10. The system according to claim 1, wherein said input means is adapted for obtaining information regarding the age of the patient and
    wherein said predetermined criteria are age-specific normative values.

11. The system according to claim 1, wherein the at least one predetermined language paradigm comprises one or more phonological tasks, semantic tasks and/or syntactic tasks.

12. The system according to claim 1, wherein the input means is a data input port configured for receiving the evoked event-related potential data as data from a remote source.

13. The system according to claim 1, wherein the input means comprises an EEG recording device adapted for recording at least electrode positions Cz and Fz.

14. The system according to claim 1, wherein the processor is positioned at a physically remote position from the patient and
    wherein the system furthermore comprises a transmission means for transmitting the evoked event-related potential data over a network.

15. A computer-implemented method for obtaining rehabilitation information for a patient suffering from aphasia, the method comprising:
    obtaining evoked event-related potential data obtained through electroencephalography of a patient, the evoked event-related potential data being evoked by providing at least one predetermined language paradigm to the patient and the evoked event-related potential data comprising amplitude, latency and source information for the evoked event-related potentials,
    processing the evoked event-related potential data comprising evaluating whether one or more of an amplitude, latency or source are within predetermined criteria for said at least one predetermined language paradigm and deriving based thereon therapy instructions to be applied to the patient, and
    outputting the therapy instructions to be applied to the patient suffering from aphasia.

16. The computer-implemented method according to claim 15, wherein said processing comprises:
    evaluating whether a latency of said evoked event-related potential data is above a first predetermined value,
    evaluating whether an amplitude of said evoked event-related potential data is above a second predetermined value, and
    evaluating whether the source is ipsilateral or contralateral homotope or non-homotope.

17. A computer program product comprising instructions which, when executed on a controller, induce a method according to claim 15.

* * * * *